(12) United States Patent
Kang

(10) Patent No.: US 10,898,755 B2
(45) Date of Patent: Jan. 26, 2021

(54) METHOD FOR PROVIDING POSTURE GUIDE AND APPARATUS THEREOF

(71) Applicant: ALYCE HEALTHCARE INC., Seongnam-si (KR)

(72) Inventor: Da Kyum Kang, Ulsan (KR)

(73) Assignee: ALYCE HEALTHCARE INC., Seongnam-si (KR)

( * ) Notice: Subject to any disclaimer, the term of this patent is extended or adjusted under 35 U.S.C. 154(b) by 0 days.

(21) Appl. No.: 16/793,871

(22) Filed: Feb. 18, 2020

(65) Prior Publication Data

US 2020/0197746 A1 Jun. 25, 2020

Related U.S. Application Data

(63) Continuation of application No. PCT/KR2018/008908, filed on Aug. 6, 2018.

(30) Foreign Application Priority Data

Aug. 18, 2017 (KR) .................. 10-2017-0104492
Jun. 13, 2018 (KR) .................. 10-2018-0067791

(51) Int. Cl.
| | |
|---|---|
| G09B 19/00 | (2006.01) |
| A63B 24/00 | (2006.01) |
| G06T 7/246 | (2017.01) |
| G06N 20/00 | (2019.01) |
| A61B 5/11 | (2006.01) |

(52) U.S. Cl.
CPC ........ *A63B 24/0006* (2013.01); *A61B 5/1116* (2013.01); *A63B 24/0062* (2013.01); *G06N 20/00* (2019.01); *G06T 7/251* (2017.01); *A63B 2024/0012* (2013.01); *A63B 2024/0068* (2013.01); *G06T 2207/10016* (2013.01)

(58) Field of Classification Search
None
See application file for complete search history.

(56) References Cited

FOREIGN PATENT DOCUMENTS

| | | |
|---|---|---|
| KR | 10-0226652 B1 | 10/1999 |
| KR | 10-0430840 B1 | 5/2004 |
| KR | 10-1498498 B1 | 3/2015 |

OTHER PUBLICATIONS

International Search Report issued in PCT/KR2018/008908; dated Nov. 9, 2018.

(Continued)

*Primary Examiner* — James B Hull
(74) *Attorney, Agent, or Firm* — Studebaker & Brackett PC

(57) ABSTRACT

According to an embodiment of the present invention, there is provided a posture guide provision method performed by an apparatus for providing posture guide using a preset machine learning model. The provision method comprises acquiring an image for a user's posture, displaying a tutoring image in a first region of a display and the acquired image in a second region of the display, extracting a feature point from the acquired image, acquiring user posture information by generating a user posture line corresponding the user's posture based on the extracted feature point, generating posture guide information for guiding the user's posture based on the tutoring image and the user posture information, and combining the acquired image and the posture guide information with each other and displaying the combination in the second region of the display.

14 Claims, 9 Drawing Sheets

(56) References Cited

OTHER PUBLICATIONS

"Grant of Patent" Office Action issued in KR 10-2018-0067791; mailed by the Korean Intellectual Property Office dated May 29, 2019.
"Notice of Final Rejection" Office Action issued in KR 10-2018-0067791; mailed by the Korean Intellectual Property Office dated Feb. 11, 2019.

METHOD FOR PROVIDING POSTURE GUIDE AND APPARATUS THEREOF

CROSS-REFERENCE TO RELATED APPLICATIONS

The present application is a continuation of International Patent Application No. PCT/KR2018/008908, filed on Aug. 6, 2018, which is based upon and claims the benefit of priority to Korean Patent Application Nos. 10-2017-0104492, filed on Aug. 18, 2017, and 10-2018-0067791, filed on Jun. 13, 2018. The disclosures of the above-listed applications are hereby incorporated by reference herein in their entirety.

TECHNICAL FIELD

The present invention relates to a method for providing posture guide and apparatus thereof. More specifically, the present invention relates to a method and an apparatus for providing a posture guide through an image analysis for a user's posture.

BACKGROUND ART

Recently, services of analyzing a video of a user's motion such as an exercise posture, a dance motion, and a rehabilitation posture, and providing feedback to a correct posture to the user have been provided. The services analyze a posture of a user by capturing the user using a 3D camera to detect a movement of the user's body joint or attaching a sensor to the user's body to extract a movement. In addition, an analysis result of the user's posture is compared with a reference posture stored in advance to provide feedback.

The services have an advantage that a user can use the services without limitation of a time and a space. However, in order to use the services, an expensive device such as a 3D camera or a sensor should be purchased. Moreover, there are inconveniences that the user installs the purchased device at an appropriate position oneself and the sensor is directly attached to the user's body. In addition, when the feedback is provided to the user in the above-described services, the reference posture stored in advance and the user's posture are simply compared with each other to provide feedback information. Accordingly, there is a disadvantage that a customized feedback for a current state of a user who is posing cannot be provided. Moreover, guide information on the user's posture cannot be dynamically changed and provided in response to the current state of the user.

Nevertheless, a service of providing customized feedback and dynamically providing guide information for a user's current state through a machine learning based user posture measurement on an image captured by a 2D camera without an expensive device is not provided.

Technical Problem

A technical problem to be solved by the present invention is to provide a method and an apparatus for measuring a user's posture using a deep learning solution and providing posture guide information to the user.

Specifically, the technical problem to be solved by the present invention is to measure a user's posture and compare a tutoring image provided to the user and the user's posture with each other to provide feedback information on the posture to the user.

Another technical problem to be solved by the present invention is to provide a method and an apparatus for analyzing a current state of a user from the user's posture and generating a user-customized tutoring image based on the analyzed current state of the user.

Still another technical problem to be solved by the present invention is to provide a method and an apparatus for comparing a tutoring image and a user's posture with each other to display real-time posture guide information required by the user.

Technical problems of the present invention are not limited to the technical problems mentioned above, and other technical problems not mentioned will be clearly understood by those skilled in the art from the following description.

Technical Solution

In order to solve the above-described technical problems, there is provided a posture guide provision method performed by an apparatus for providing posture guide using a preset machine learning model, the method including: acquiring an image for a user's posture; displaying a tutoring image in a first region of a display and the acquired image in a second region of the display; extracting a feature point from the acquired image; acquiring user posture information by generating a user posture line corresponding the user's posture based on the extracted feature point; generating posture guide information for guiding the user's posture based on the tutoring image and the user posture information; and combining the acquired image and the posture guide information with each other and displaying the combination in the second region of the display.

In an embodiment, the generating of the posture guide information for guiding the user's posture may include extracting a tutoring line from the tutoring image, causing the user posture line to correspond to the tutoring line, scaling the corresponding user posture line based on the tutoring line, and generating the posture guide information based on a result of the scaling.

In an embodiment, the generating of the posture guide information for guiding the user's posture may include extracting tutoring lines from the tutoring image, identifying a posture stop line out of the tutoring lines, extracting information of a line corresponding to the posture stop line out of the user posture lines, and generating the posture guide information based on the posture stop line and the information of the corresponding line.

In an embodiment, the generating of the posture guide information for guiding the user's posture may include extracting a tutoring line from the tutoring image, extracting an object line corresponding to the tutoring line out of the user posture lines, and generating, when an angle of the tutoring line is changed by the tutoring motion, a tutoring target line corresponding to the tutoring line having the changed angle.

In an embodiment, the combining of the acquired image and the posture guide information with each other and displaying of the combination may include displaying the generated tutoring target line in the second region, generating a guide line for guiding the object line toward the tutoring target line based on an angle difference between the generated tutoring target line and the object line, and displaying the generated guide line in the second region.

In an embodiment, the displaying of the generated guide line in the second region may include changing at least one of a length and a direction in response to a movement of the object line based on the generated tutoring target line and displaying the guide line.

In an embodiment, the displaying of the generated guide line in the second region may include determining whether or not the object line and the tutoring target line are matched with each other according to the movement of the object line, generating feedback information for the user's posture based on a result of the determination, and displaying the generated feedback information.

In an embodiment, the displaying of the feedback information may include changing and displaying a color of the tutoring target line according to the object line and the tutoring target line overlapping each other during a preset time.

In an embodiment, the displaying of the feedback information may include calculating first an angle difference between the object line and the tutoring target line after the movement of the object line occurs, generating a first correction tutoring image for the tutoring image when the first calculated angle difference exceeds a preset range, and replacing the tutoring image displayed in the first region with the first correction tutoring image and outputting the replaced first correction tutoring image.

In an embodiment, the determining of whether or not the object line and the tutoring target line are matched with each other may include calculating first an angle difference between the object line and the tutoring target line after the movement of the object line occurs, counting the number of times the first calculated angle difference has a value within a preset range, and determining whether or not the object line and the tutoring target line are matched with each other based on the counted number of times.

In an embodiment, the method may further include extracting a first correction tutoring line from the first correction tutoring image, generating, when an angle of the first correction tutoring line is changed by a tutoring motion, a first correction tutoring target line corresponding to a first correction tutoring line having the changed angle; displaying the generated first correction tutoring target line in the second region; calculating second an angle difference between the object line and the first correction tutoring target line after the movement of the object line occurs; and regenerating the posture guide information based on the second calculated angle difference.

In an embodiment, the regenerating of the posture guide information may include generating a second correction tutoring image for the tutoring image when the second calculated angle difference is within a preset range.

In an embodiment, the generating of the first correction tutoring image may comprise acquiring biological information of the user from a biological information recognizer, and generating the first correction tutoring image based on the acquired biological information.

In an embodiment, the determining of whether or not the object line and the tutoring target line are matched with each other based on the counted number of times may include acquiring biological information of the user from the biological information recognizer when the counted number of times is less than a preset number of times, and the generating of the feedback information for the user's posture may include generating the feedback information based on the acquired biological information.

In order to solve the above-described technical problems, there is provided a posture guide provision program stored in a recording medium, the program, in a combination of a computing device, executing: acquiring an image for a user's posture; displaying a tutoring image in a first region of a display and the acquired image in a second region of the display; extracting a feature point from the acquired image using the preset machine learning model; acquiring user posture information by generating a user posture line corresponding the user's posture based on the extracted feature point; generating posture guide information for guiding the user's posture based on the tutoring image and the user posture information; and combining the acquired image and the posture guide information with each other and displaying the combination in the second region of the display.

In order to solve the above-described technical problems, there is provided an apparatus for providing posture guide including: one or more processors; a camera which acquires an image for a user's posture; a display which displays a tutoring image in a first region and displays the acquired image in a second region; a memory which loads a computer program executed by the processor; and a storage which stores the computer program, in which the computer program comprises an operation of extracting a feature point from the acquired image using a preset machine learning model, an operation of acquiring user posture information by generating a user posture line corresponding to the user's posture based on the extracted feature point, an operation of generating posture guide information for guiding the user's posture based on the tutoring image and the user posture information, and an operation of combining the acquired image and the posture guide information with each other and displaying the combination in the second region of the display.

Advantageous Effects

According to an embodiment of the present invention, even though a user does not purchase a separate device, a user applies a posture guide solution to a 2D camera and a display device to use a service. Moreover, the solution can be applied to a posture guide service of a rehabilitation exercise field as well as a simple exercise and a dance motion, and can be applied to all cases requiring measurements of a posture and motion of the user.

In addition, according to another embodiment, a visual guide in real time is provided to a degree which needs to be corrected in the posture of the user, and thus, a service that allows the user to correct the posture in real time can be provided.

Moreover, according to still another embodiment, the tutoring posture being provided is corrected by analyzing a current condition of the user, and thus, an optimal posture is guided to the user.

DETAILED DESCRIPTION

Figure 1:
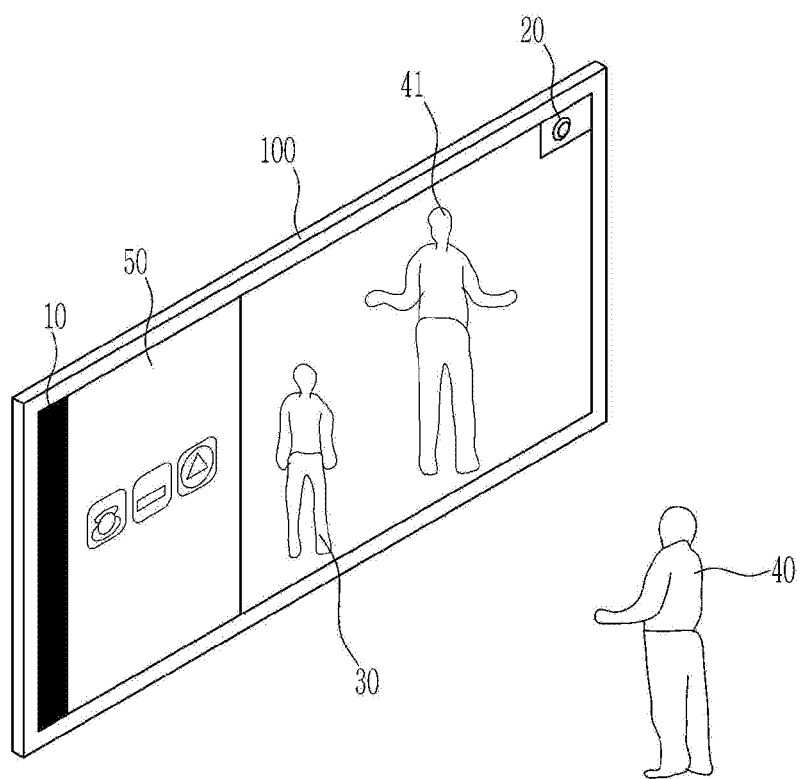
FIG. 1 is a conceptual diagram of an apparatus for providing posture guide according to an embodiment of the present invention.

Hereinafter, exemplary embodiments of the present invention will be described in detail with reference to the accompanying drawings. Advantages and features of the present invention, and methods of achieving the same will be apparent with reference to embodiments described below in detail with reference to the accompanying drawings. However, the present invention is not limited to the embodiments disclosed below, but can be implemented in various forms, and the present embodiments are merely provided to complete the disclosure of the present invention and to fully inform the scope of the invention to those skilled in the art, and the present invention is only defined by the scope of the claims. The same reference numerals refer to the same elements throughout.

Unless otherwise defined, all terms (including technical and scientific terms) used in the present specification may be used in a sense which can be commonly understood by those skilled in the art. In addition, terms which are defined in a commonly used dictionary are not ideally or excessively interpreted unless they are specifically defined clearly. The terms used in the present specification is for the purpose of describing particular embodiments only and is not intended to be limiting of the invention. In the present specification, singular forms also include plural forms unless specifically stated otherwise in the phrase.

In the present specification, an image for a user's posture and a tutoring image may be a video including a plurality of image frames. For example, the tutoring image may be an image in which a tutor repeats a specific motion, and according to some embodiments, the specific motion may be any one of yoga motion, a Pilates motion, a rehabilitation exercise motion, a muscle exercise motion, a dance motion, and a game motion.

FIG. 1 is a conceptual diagram of an apparatus for providing posture guide according to an embodiment of the present invention.

Referring to FIG. 1, an apparatus for providing posture guide 100 may be a fixed computing device such as a personal desktop PC or a smart TV. In particular, the apparatus for providing posture guide 100 may be a multi-media playback device including a display 10 and a camera 20. However, the embodiment of the present invention is not limited to this. That is, the apparatus for providing posture guide 100 may be a mobile computing device such as a smart phone, a tablet PC, a laptop PC, or a PDA, or a computing device such as a virtual reality (VR) imaging device or an augmented reality (AR) imaging device, and may be any apparatus for providing posture guide 100 as long as it can display the image for the user's posture.

The apparatus for providing posture guide 100 may acquire an image of a user 40 through the camera 20 and display the acquired user image 41 on the display 10. In addition, the apparatus for providing posture guide 100 may display a tutoring image 30 for tutoring the posture to the user. The tutoring image 30 may be an image of a virtual tutor generated and output by executing a program stored in advance, or may be an image which is reproduced after a tutoring image of an actual tutor is captured. Alternatively, the tutoring image 30 may be an image processed based on the tutoring image of the actual tutor.

The apparatus for providing posture guide 100 acquires the user posture image 41 of the user 40 who views the tutoring image 30 and follows the tutoring posture, and may provide a matching degree of the user posture image 41 with respect to the tutoring image 30, as feedback information 50. In FIG. 1, particularly, a case where the tutoring image 30 and the user posture image 41 are simultaneously displayed through the display 10 is illustrated. A case where the feedback information 50 is located on right sides of the tutoring image 30 and the user posture image 41 is illustrated. However, the embodiment of the present invention is not limited thereto, and the feedback information 50 may be located below the tutoring image 30 and the user posture image 41.

In addition to the above-described configurations, the apparatus for providing posture guide 100 of FIG. 1 may be connected to or communicate with a wearable device or a physical contact sensor for acquiring biometric information of a user. For example, the apparatus for providing posture guide 100 may access or communicate with an EMG measuring device to collect state information such as muscle activity information of the user. In addition, a case where the apparatus for providing posture guide 100 of FIG. 1 is integrated with the camera 20 and the display 10 is illustrated as an example. However, according to another embodiment of the present invention, the camera 20 and the display 10 may be separated from the 100. The camera 20 and the display 10 may not be a specialized device for the apparatus for providing posture guide 100 according to the embodiment of the present invention, and may be applied to the apparatus for providing posture guide 100 as a general-purpose device.

Figure 2:
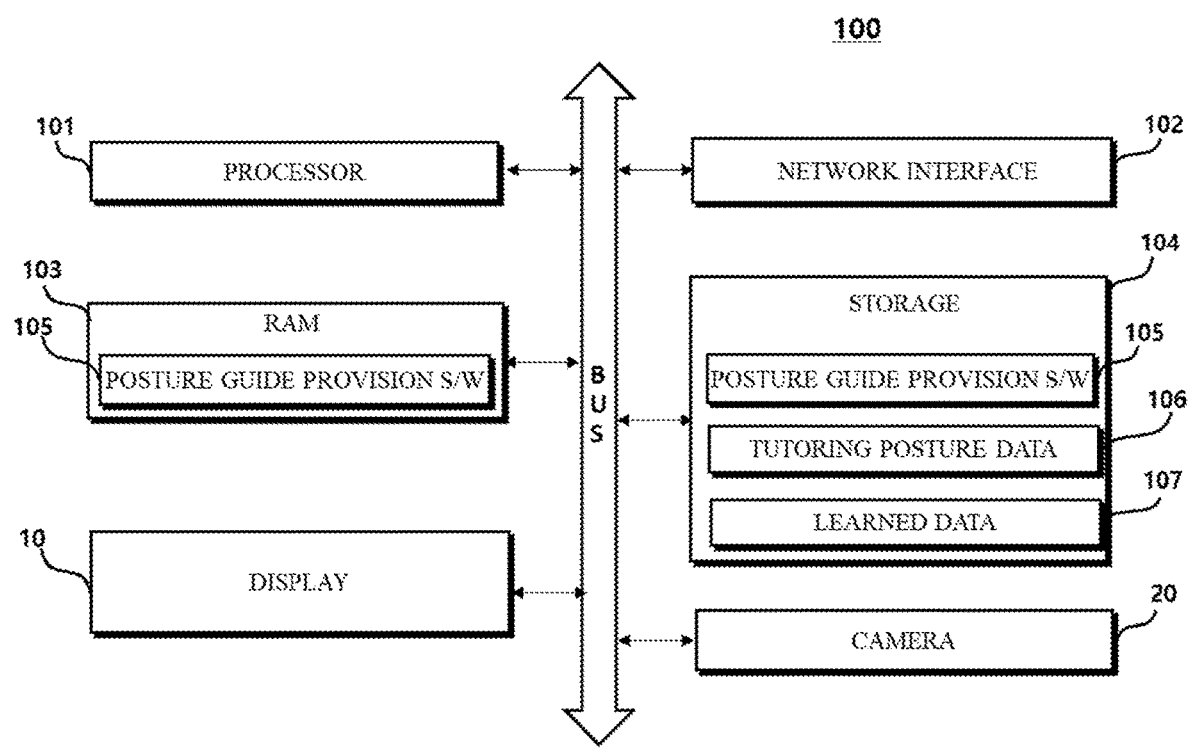
FIG. 2 is a block diagram of an apparatus for providing posture guide according to another embodiment of the present invention.

Next, the apparatus for providing posture guide 100 will be described in more detail with reference to FIG. 2. FIG. 2 is a block diagram of a apparatus for providing posture guide 100 according to another embodiment of the present invention. In particular, in FIG. 2, the apparatus for providing posture guide 100 includes a camera 20 and a display 10 as components.

The apparatus for providing posture guide 100 may include one or more processors 101, a network interface 102 to which an external device is connected to or which communicates with the external device, a memory for loading a computer program executed by the processor 101, and a storage 104 for storing the computer program.

The processor 101 controls the overall motion of each configuration of the apparatus for providing posture guide 100. The processor 101 may include a central processing unit (CPU), a micro-processor unit (MPU), a micro controller unit (MCU), or any type of processor well known in the art. In addition, the processor 101 may perform a calculation on at least one application or program for executing a method according to an embodiment of the present invention. The apparatus for providing posture guide 100 may include one or more processors.

The network interface 102 supports wired and wireless Internet communication of the apparatus for providing posture guide 100. In addition, the network interface 102 may support various communication methods in addition to the Internet, which is a public communication network. Moreover, the network interface 102 may provide a connection with the external device. To this end, the network interface 102 may include at least one of a communication module and a connection terminal well known in the art. Here, the external device may be a sensor for measuring the EMG of the user, a wearable device for measuring biometric information of the user, or a physical contact sensor device.

The memory 103 stores various data, commands and/or information. The memory 103 may load one or more programs 105 from the storage 104 to execute the method according to the embodiment of the present invention. RAM is shown as an example of the memory 103 in FIG. 3.

Figure 3:
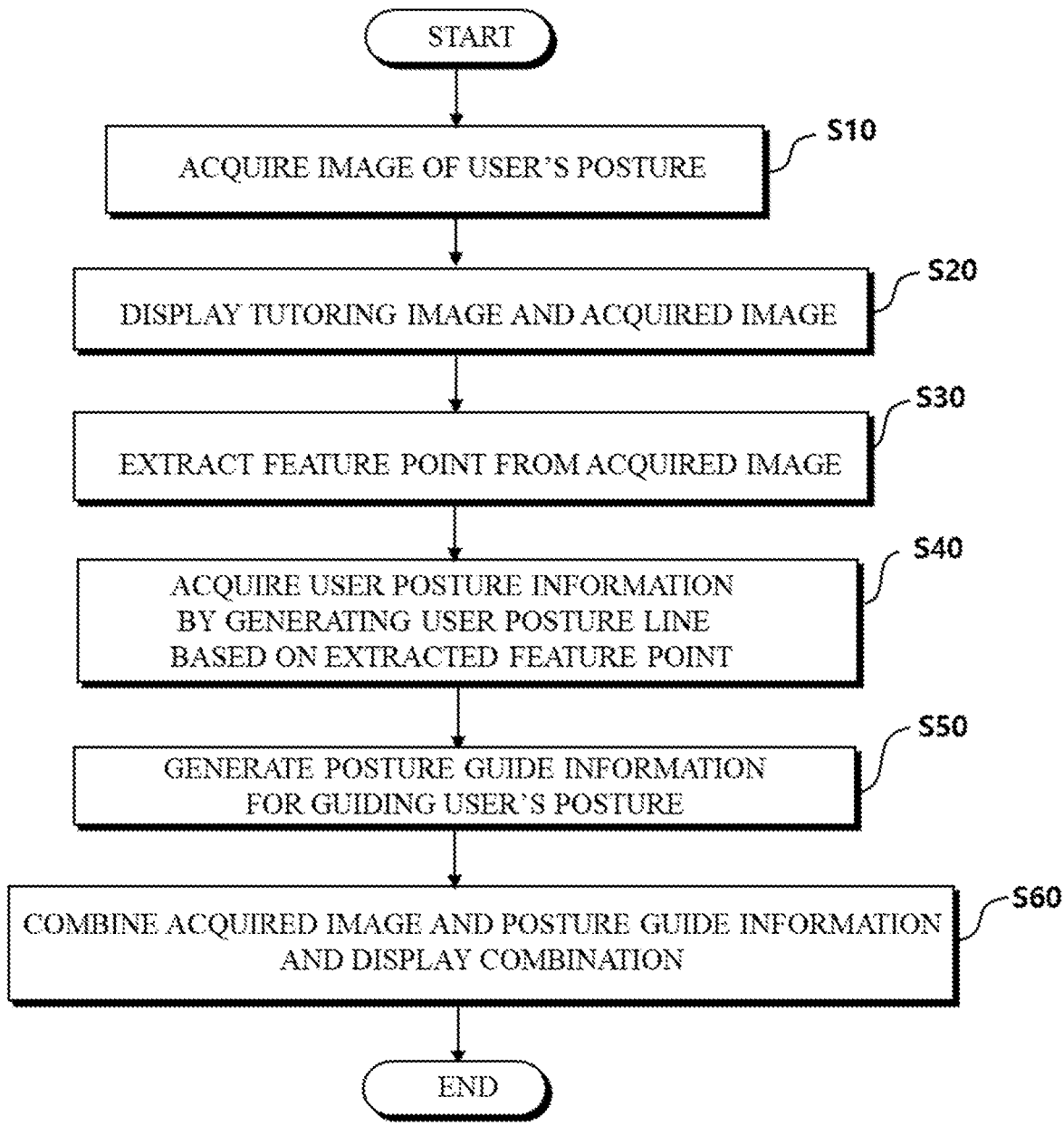
FIG. 3 is a flowchart of a posture guide provision method according to still another embodiment of the present invention.

The storage 104 may non-temporarily store one or more programs 105, tutoring posture data 106, and training data 107. In FIG. 3, posture guide provision software 105 is shown as an example of the one or more programs 105. The posture guide provision software 105 may be referred to as a posture guide provision program.

The storage 104 may include a non-volatile memory such as a Read Only Memory (ROM), an Erasable Programmable ROM (EPROM), an Electrically Erasable Programmable ROM (EEPROM), or a flash memory, a hard disk, a removable disk, or any type of computer readable recording medium well known in the art to which the present invention pertains.

The posture guide providing software 105 may support the apparatus for providing posture guide 100 so that the apparatus for providing posture guide 100 provides various user interfaces (UIs) through the display 10 according to an embodiment of the present invention. In addition, according to an embodiment of the present invention, the posture guide providing software 105 may include a machine learning model generated based on the learning data 107 described later.

As the machine learning model is driven by the processor 101, a plurality of user posture image frames is analyzed to extract a feature point. Herein, the machine learning model may include an artificial neural network, and may be configured to include at least one of a convolution neural network (CNN), an auto encoder, a feedforward neural network, and a radial basis function network, a kohonen self-organizing network, and a recurrent neural network (RNN).

For example, when the machine learning model includes the convolutional neural network, as the machine learning model is driven by the processor 101, the feature values of the user posture image 41 are filtered out, and only a specific value out of several image pixels is newly taken through a convolutional calculation. By repeatedly learning this, a desired feature point can be extracted.

The feature point may be a portion of a body which is a joint portion of the user's body. The feature point is a portion of the body which can be identified by the processor 101 executing the posture guide provision program 105, and for example, the feature point may be a point corresponding to an eye, nose, mouth, shoulder, elbow, wrist, chest, pelvis, knee, ankle, or the like which is a portion of a body of a human or a point constituting a line corresponding to a portion of the body.

The learning data 107 may be feature point extraction result data accumulated through the machine learning. Alternatively, the learning data 107 may be feed data as feature point data for machine learning modeling.

The posture guide provision software 105 is an algorithm in which the machine learning model is extended, and by driving the posture guide provision software 105, the apparatus for providing posture guide 100 may perform the following functions.

For example, the apparatus for providing posture guide 100 may recognize, analyze, and connect a feature point using a confidence map. In addition, for example, the apparatus for providing posture guide 100 may analyze directionality and similarity based on the feature points using part affinity fields (PAFs) so that the feature points are associated with each other. That is, the apparatus for providing posture guide 100 may generate a line by associating and connecting respective feature points, and the generated line corresponds to a bone of the user's body. For example, a line connecting a feature point of a wrist and a feature point of an elbow to each other corresponds to a bone of an arm below an elbow of a human.

In addition, for example, the apparatus for providing posture guide 100 may analyze a movement of the feature point using a Greedy algorithm. By continuously tracking the line, the apparatus for providing posture guide 100 may identify a movement of a line corresponding to the user's posture.

Here, the confidence map refers to a function of classifying and displaying elasticity data of a tissue according to reliability. In addition, the Part Affinity Fields (PAF) refers to a method of associating a body portion with an individual in an image using a non-parameter. In addition, the Greedy algorithm is an algorithm which solves the whole problem by making greedy choices every moment when solving the whole problem.

The machine learning model may extract feature points corresponding to a plurality of portions of the user's body on each frame of the user image continuously input to the apparatus for providing posture guide 100, and analyze association between the feature points to confirm the extracted feature point. Accordingly, the machine learning model may connect the confirmed feature point information to generate the line.

The tutoring posture data 106 may be continuous posture data which includes a plurality of tutor image frames. The tutoring posture data 106 may include the feature point and/or the line information on a tutor image.

The apparatus for providing posture guide 100 executes the posture guide provision software 105, and thus, the apparatus for providing posture guide 100 may generate or correct a tutoring image by using the tutoring posture data 106.

The apparatus for providing posture guide 100 executes the posture guide provision software 105, and thus, the apparatus for providing posture guide 100 may scale the user posture image based on a tutor image on the tutoring posture data 106.

In addition, although not illustrated, the apparatus for providing posture guide 100 may include an audio output unit for voice-outputting feedback information according to an embodiment of the present invention.

Figure 4:
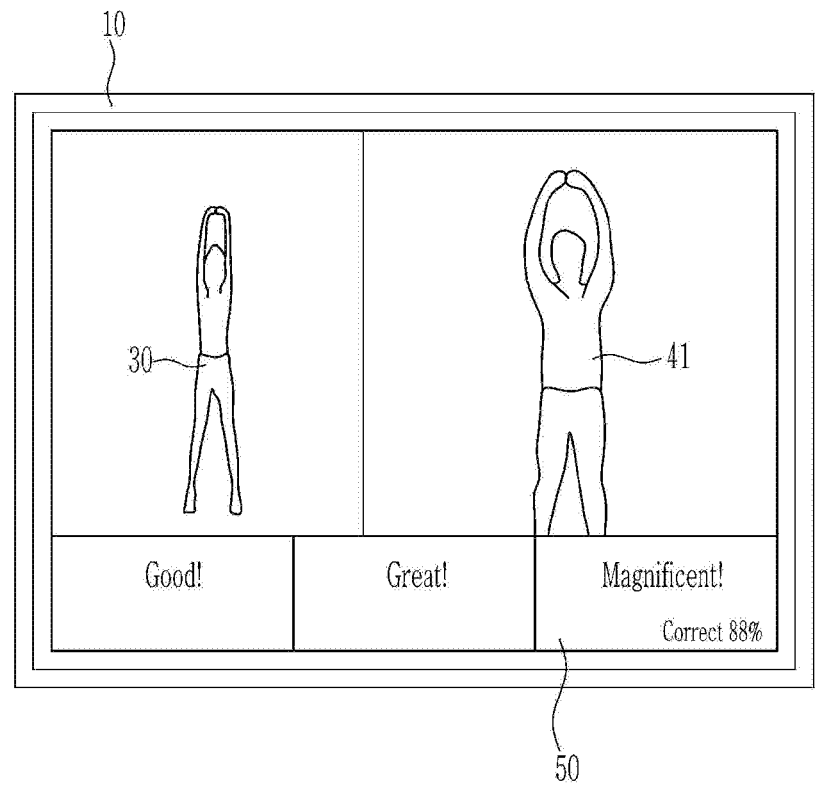
FIG. 4 is an exemplary diagram for explaining a tutoring image and an image for a user's posture, referred to in some embodiments of the present invention.

FIG. 3 is a flowchart of a posture guide provision method according to still another embodiment of the present invention. FIG. 4 is an exemplary diagram for explaining the tutoring image and the image for the user's posture, referred to in some embodiments of the present invention.

The following steps are performed by the apparatus for providing posture guide 100, and in particular, the following steps are performed by the processor 101 performing a calculation according to the posture guide provision software 105. Moreover, particularly, FIG. 4 illustrates a case where a first region of the display 10 is a left region in which the tutor image is displayed and a second region thereof is a right region in which the user posture image is displayed, as an example. In addition, FIG. 4 illustrates a case where a feedback degree is displayed in regions below the first region and the second region.

Referring to FIG. 3, the apparatus for providing posture guide 100 may acquire the image of the user's posture through the camera 20 (S10).

Referring to FIGS. 3 and 4, the apparatus for providing posture guide 100 may display the tutoring image 30 in the first area of the display 10 and display the acquired image 41 in the second area (S20).

Next, the apparatus for providing posture guide 100 may extract the feature point from the acquired image 41 (S30). In addition, the apparatus for providing posture guide 100 acquires user posture information by generating a user posture line corresponding to the user's posture based on the extracted feature point (S40). Here, the user posture information may be information such as an angle and a length between skeletons constituting the user's posture. The user posture line will be described later with reference to FIG. 6.

In addition, the apparatus for providing posture guide 100 may generate posture guide information for guiding the user's posture (S50), and combine the acquired user posture image and posture guide information with each other to display the combination (S60).

Figure 5:
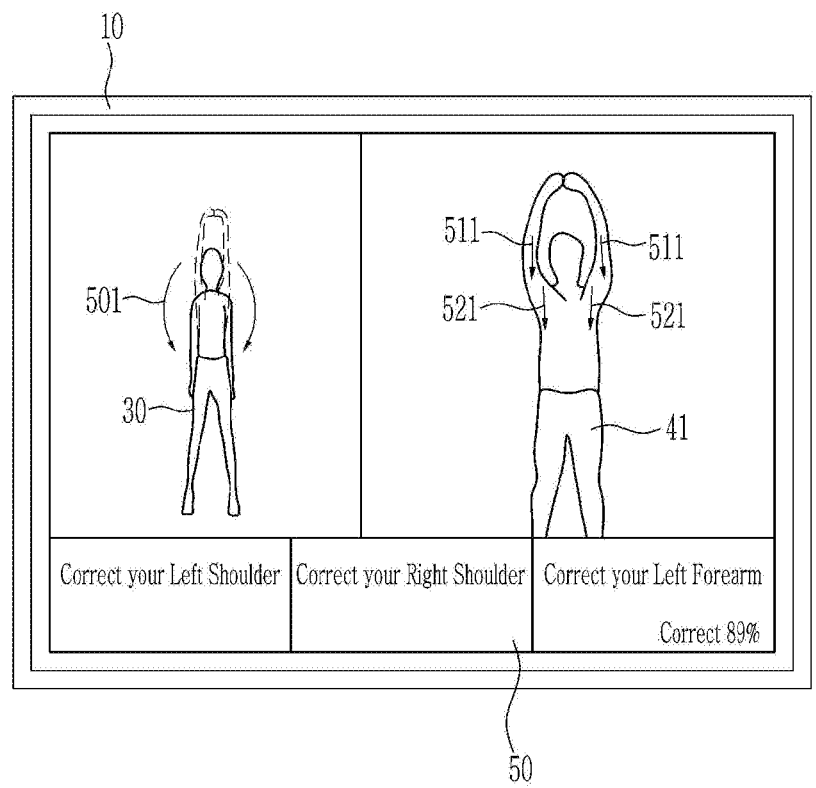
FIGS. 5 and 6 are exemplary diagrams for explaining guide information, referred to in some embodiments of the present invention.
Figure 6:
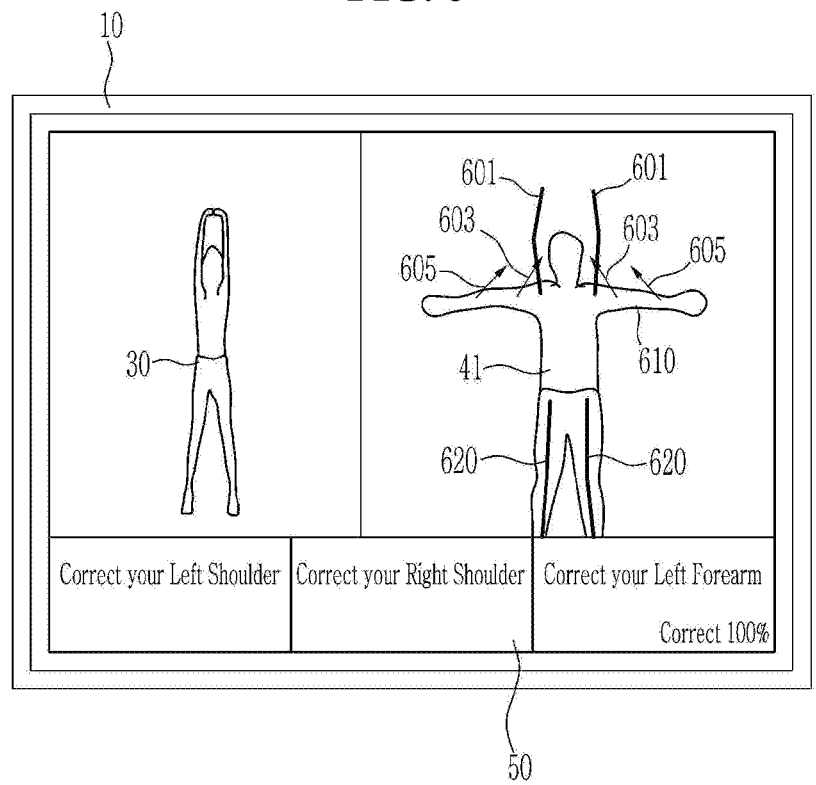

Steps S50 and S60 will be described in detail with reference to FIGS. 5 and 6. FIGS. 5 and 6 are exemplary diagrams for explaining the posture guide information, referred to in some embodiments of the present invention.

Referring to FIG. 5, the apparatus for providing posture guide 100 may display a tutoring motion in the tutoring image 30. In particular, as an example of a tutoring motion 501, FIG. 5 illustrates a case where the tutor changes a motion from a motion (hereinafter, referred to as a first motion) in which the tutor raises both arms to a motion (hereinafter, referred to as a second motion) in which the tutor lowers both arms.

The apparatus for providing posture guide 100 may identify the tutoring motion 501, and if the user's posture is changed in response to the tutoring motion 501, the apparatus for providing posture guide 100 may acquire an image for the change and display a change of the user posture image 41. In this case, the apparatus for providing posture guide 100 may display the image for the user's posture in the second region and display posture guide information for both arms of the user. In FIG. 5, as an example of the posture guide information, posture guide lines 511 and 521 are illustrated, and the posture guide lines 511 and posture guide lines 521 are lines for guiding a movement of the skeleton which forms the skeletal structure of the arm, respectively. In particular, although each guide line is indicated by an arrow having a direction, the embodiment of the present invention is not limited thereto.

Meanwhile, referring to FIGS. 5 and 6, the apparatus for providing posture guide 100 may display the feedback information. In this case, the feedback information may include textual guide information while the user posture image is moving. For example, a text for correcting a right shoulder posture may be displayed as guide information.

Meanwhile, the feedback information when the user posture image is stopped for a predetermined time or more may include a matching ratio between the tutoring image and the user posture image. When the user posture image is stopped for a predetermined time or more, the apparatus for providing posture guide 100 may determine that the user moves along the tutoring image and the motion is completed. Accordingly, the apparatus for providing posture guide 100 may analyze a degree of similarity between the tutoring image and the user posture image, and display information numerically indicating the degree of similarity. The feedback information may include a matching rate between a time required for the tutoring image to change from the first motion to the second motion according to the tutoring motion and a time required to change the user posture image in response thereto.

Referring to FIG. 6, the posture guide information may include tutoring target lines 601 as well as guide lines 603 and 605. FIG. 6 illustrates a case where as the tutor raises both arms on the tutoring image 30, the tutoring target lines 601 on the user posture image 41 are displayed and the guidelines 603 and 605 for the user posture image 41 are displayed.

The tutoring target line is a line corresponding to a tutoring line extracted based on the posture of the tutor on the tutoring image 30 displayed in the first region. That is, the tutoring line is a motion line to be followed by the user posture image. However, the tutoring line is displayed in the first region, which may be inconvenient to directly compare with the user posture image. Accordingly, the apparatus for providing posture guide 100 may take the tutoring target lines 601 corresponding to the tutoring line of the first region as a target line of the user posture image, and combine the tutoring target lines 601 and the user posture image 41 acquired through the camera 20 and display the combination on the second region. In other words, the tutoring target line 601 may be a line of which the tutoring line is adjusted based on the user posture image 41 by the apparatus for providing posture guide 100.

In this case, when an angle difference between the user posture image 41 and the tutoring target line 601 occurs, the apparatus for providing posture guide 100 may display the guide lines 603 and 605 so that the user posture image 41 follows the tutoring target line 601.

In addition, when an angle change between one tutoring line and the other tutoring line occurs on the tutoring image 30 by the tutoring motion, the apparatus for providing posture guide 100 may recognize a time when the angle change is continued as one tutoring motion limitation time. The apparatus for providing posture guide 100 may measure a time when the user posture image 41 moves along the tutoring target line 601 to determine whether the user follows the guide of the tutoring motion.

Meanwhile, in FIG. 6, user posture lines 620 are illustrated on the user posture image 41. The user posture line is a line obtained by connecting the feature points extracted from the user posture image, and the apparatus for providing posture guide 100 may generate the user posture line according to the method described above with reference to FIG. 2.

Figure 7:
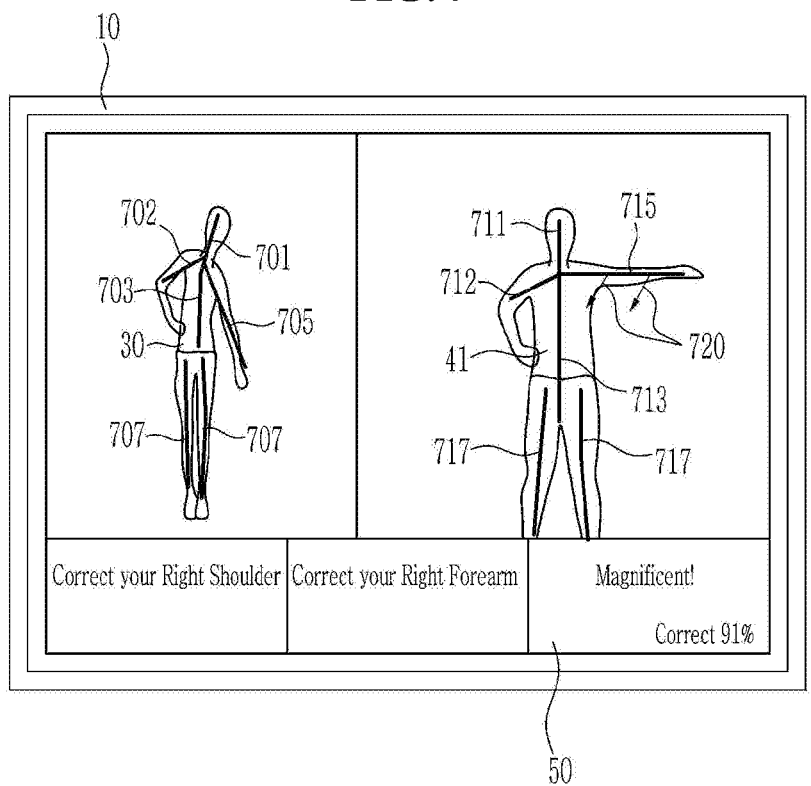
FIGS. 7 and 8 are exemplary diagrams for explaining posture guide information generated based on still posture information, referred to in some embodiments of the present invention.
Figure 8:
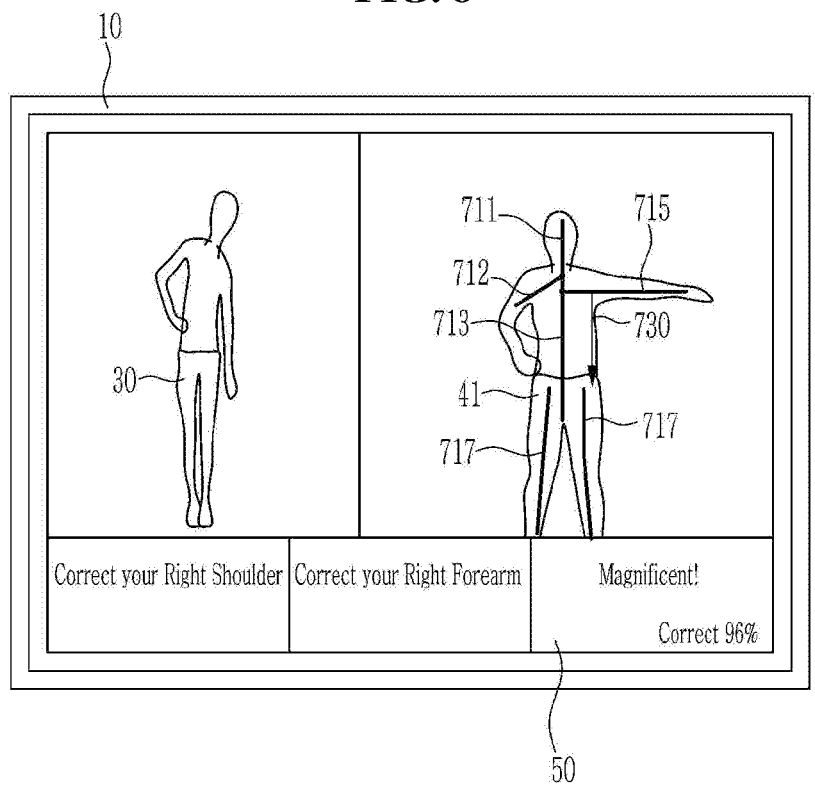

FIGS. 7 and 8 are exemplary diagrams for explaining posture guide information generated based on still posture information, referred to in some embodiments of the present invention.

In Step S50 of FIG. 3, the apparatus for providing posture guide 100 may extract the tutoring line from the tutoring image 30 and cause the user posture line to correspond with the tutoring line.

Referring to FIG. 7, the apparatus for providing posture guide 100 may extract tutoring lines 701, 702, 703, 705, and 707 from the tutoring image 30, and may extract user posture lines 711, 712, 713, 715, and 717 from the user posture image 41. Next, the apparatus for providing posture guide 100 may cause the user posture lines 711, 712, 713, 715, and 717 to correspond with the tutoring lines 701, 702, 703, 705, and 707, respectively.

In this case, the corresponding user posture line and the tutoring line have different lengths and ratios. That is, the tutoring line 703 and the user posture line 713 corresponding to a torso have different lengths, and accordingly, the ratio of both is different. In addition, a ratio of mutual lengths of the tutoring line 703 for the body and the tutoring line 705 for the arm is different from a ratio of mutual lengths of the user posture line 713 for the torso and the user posture line 715 for the arm. In this case, even if the user moves by the amount of exercise when a specific angle is generated between the tutoring line 703 for the torso and the tutoring line 705 for the arm according to the tutoring motion and the same movement as the tutoring motion, amounts of exercise generated between the user posture line 713 for the torso and the user posture line 715 for the arm may be different from each other.

In the case where the posture and the amount of exercise of the tutoring motion have a significant impact on the user's health, such as a rehabilitation exercise, the apparatus for providing posture guide 100 may scale the user posture line based on the tutoring line in order to prevent side effects caused by inappropriate posture or excessive exercise. That is, the length and ratio of each user posture line may be scaled according to the length and ratio of the tutoring line, and after this scaling, the apparatus for providing posture guide 100 may generate posture guide information on the user posture line based on the scaling. According to an embodiment, the guide line and the tutoring target line described in FIGS. 5 and 6 may be changed to be customized based on the user posture image. More specifically, angles of the tutoring line and the tutoring target line after the tutoring motion may be different from each other.

According to another embodiment of the present invention, the apparatus for providing posture guide 100 may identify the tutoring line 705 to which the tutoring motion is applied on the tutoring image. In addition, the apparatus for providing posture guide 100 may extract the object line 715 corresponding to the identified tutoring line 705 out of the user posture lines. Here, the object line refers to a user posture line which is a target of the movement along the tutoring motion. The apparatus for providing posture guide 100 may generate the tutoring target line corresponding to the tutoring line 705 when the angle of the tutoring line 705 is changed by the tutoring motion.

In FIG. 8, the tutoring target line 730 is illustrated as an example. The apparatus for providing posture guide 100 may display the tutoring target line 730 generated in the second region.

The apparatus for providing posture guide 100 may display the tutoring target line generated in the second region in Step S60 of FIG. 3. In addition, the apparatus for providing posture guide 100 may generate a guide line for guiding the object line toward the tutoring target line, based on an angle difference between the generated tutoring target line and the object line.

In FIG. 7, a guide line 720 is illustrated as an example. The apparatus for providing posture guide 100 may display the guide line 720 generated in the second region.

According to still another embodiment of the present invention, the apparatus for providing posture guide 100 may identify a posture stop line out of the tutoring lines 701, 702, 703, 705, and 707. In FIG. 7, the posture stop line is the tutoring lines 701, 702, 703, and 707 excluding the tutoring line 705. The apparatus for providing posture guide 100 may extract information of the user posture lines 711, 712, 713, and 717 corresponding to the posture stop lines.

The apparatus for providing posture guide 100 may generate posture guide information based on the information of the posture stop line and the corresponding line. Referring to FIG. 7, an angle is formed between the tutoring line 701 and the tutoring line 703 out of the posture stop line, and the user posture line 711 and the user posture line 713 form a straight line. That is, a dynamic structure of the remaining posture stop line other than the motion line 705 is different from a dynamic structure of the remaining user posture line other than the object line 715. In this case, even if the tutoring motions are the same as each other, the amount of exercise of the tutor on the tutoring image and the amount of exercise on the user posture image may be different from each other. The apparatus for providing posture guide 100 may calculate an amount of exercise suitable for the user in consideration of different dynamic structures, and may adjust at least one of the lengths and the angles of the guide line and the tutor target guide based on the calculated amount of exercise.

So far, as a method of generating the posture guide information, the length, ratio, and angle of the tutoring target line and the user posture line are described. However, the embodiment of the present invention is not limited thereto. The apparatus for providing posture guide 100 may determine the matching ratio between the tutoring target line and the user posture line and generate the posture guide information by comparing feature point coordinates on the tutoring target line and the user posture line with each other or by dividing a screen into pixel units.

Referring to FIGS. 7 and 8, the apparatus for providing posture guide 100 may display the guide line 720 generated in the second region, and may display the guide line 720 by changing at least one of the length and the direction in response to the movement of the object line 715 based on the generated tutoring target line 730. That is, based on the tutoring target line, as the user moves, the object line 715 approaches the tutoring target line, and the angle decreases. In this case, the guide line 720 is gradually shorter, the angle is also reduced.

Subsequently, as the object line 715 approaches the tutoring target line, the apparatus for providing posture guide 100 may determine whether or not the object line and the tutoring target line match. The apparatus for providing posture guide 100 may generate feedback information about the user's posture and display the feedback information based on a determination result of the matching.

In this case, the apparatus for providing posture guide 100 may change and display a color of the tutoring target line as the object line 715 and the tutoring target line overlap each other for a preset time. That is, when the user moves along the tutoring motion, the user posture line is located at the tutoring target line, and at this time, when the user tutoring posture line is located at the tutoring target line over the preset time, the apparatus for providing posture guide 100 may change a color of the tutoring target guide of the first color to a second color and display the second color.

Figure 9:
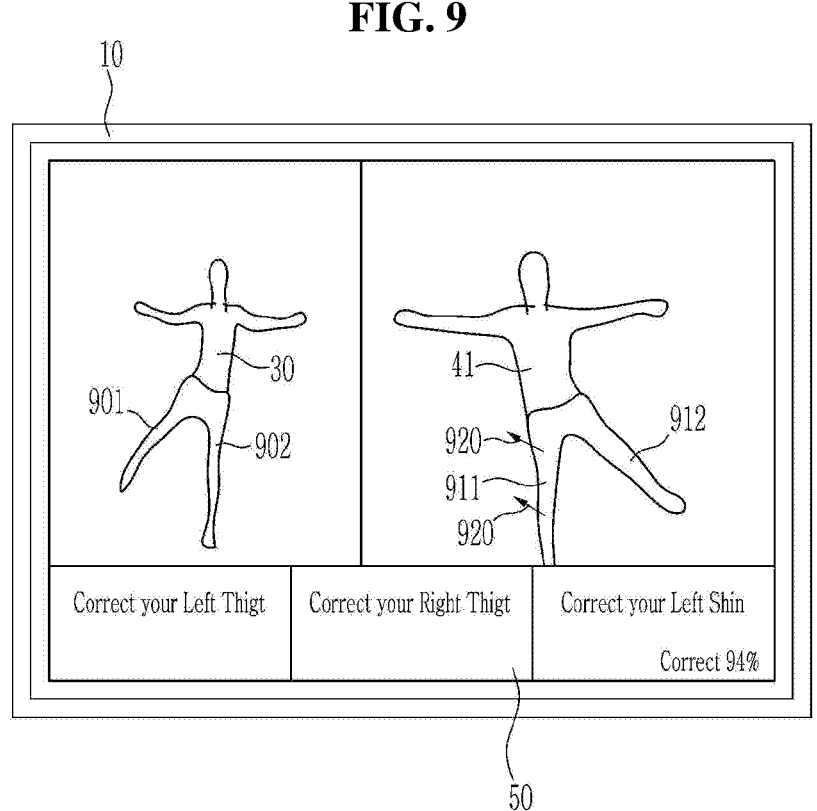
FIGS. 9 and 10 are exemplary diagrams for explaining a plurality of object lines, referred to in some embodiments of the present invention.
Figure 10:
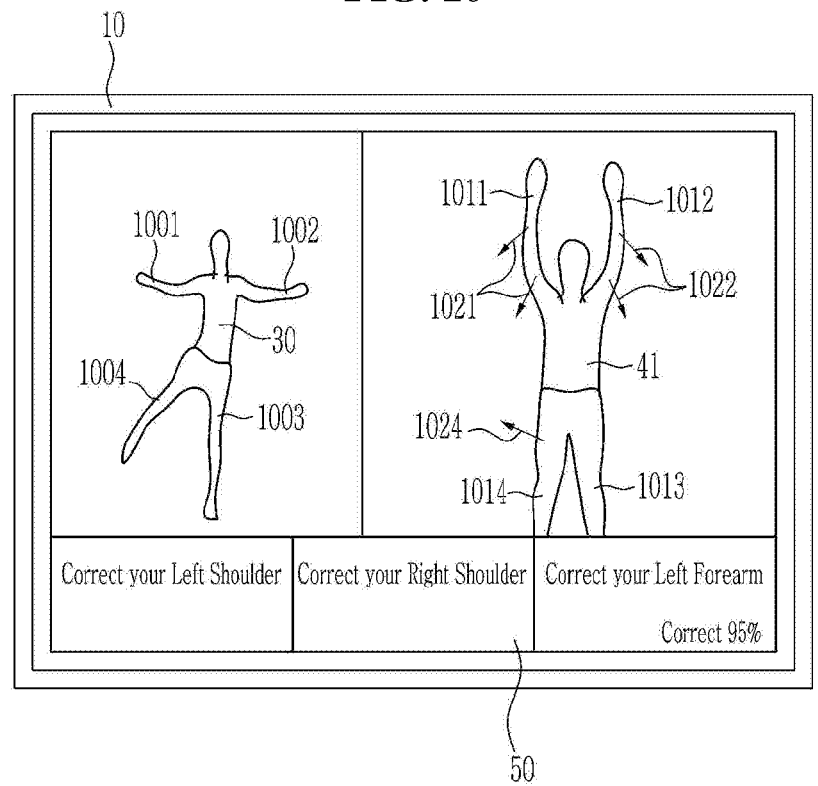

FIGS. 9 and 10 are exemplary diagrams for explaining a plurality of object lines, referred to in some embodiments of the present invention.

Referring to FIG. 9, the apparatus for providing posture guide 100 may identify wrong because the user posture line 912 moves even though the user posture line corresponding to the tutoring line 901 is the object line 911. In this case, the apparatus for providing posture guide 100 may identify the object line 911 and generate guide information for the object line. That is, the apparatus for providing posture guide 100 may control the object line 911 so that the guide line 920 for the object line 911 is displayed.

Referring to FIG. 10, the user posture image illustrated in FIG. 9 is changed, and a case where the user raises both arms and lowers legs is illustrated as an example.

As in the case of FIG. 9, the apparatus for providing posture guide 100 may generate the posture guide information on an object line 1014. In addition, the apparatus for providing posture guide 100 may identify lines 1011 and 1012 corresponding to the user's arms, which are not the object lines in FIG. 9, as the object lines. That is, the apparatus for providing posture guide 100 may identify the new object lines 1011 and 1012 in response to the posture change of the user compared to FIG. 9, and generate the posture guide information on the object lines 1011 and 1012. In FIG. 10, guide lines 1021 and 1022 are illustrated as an example of the generated posture guide information.

Figure 11:
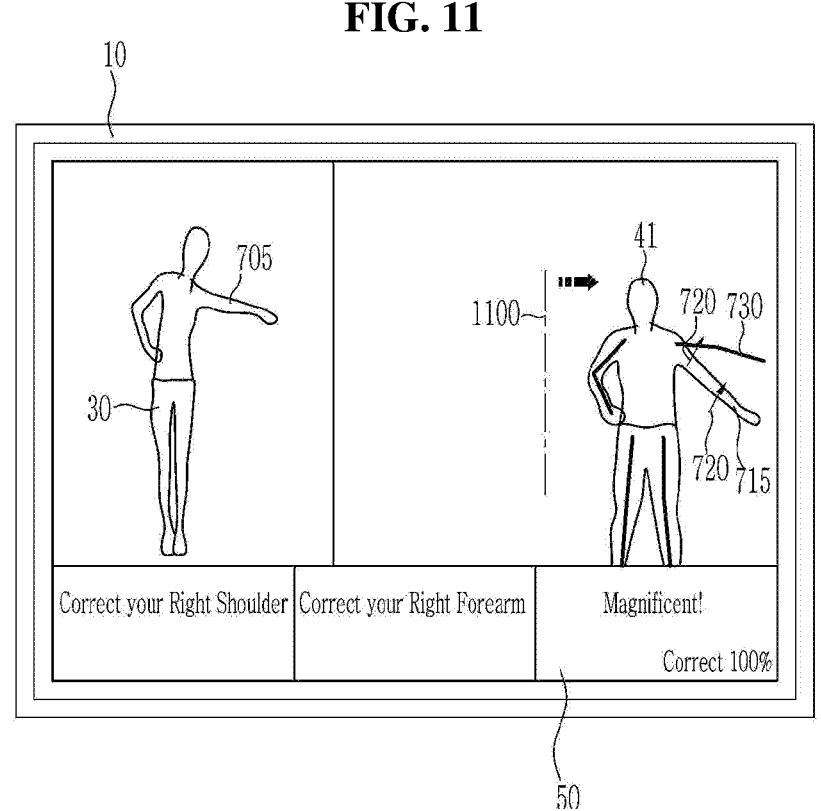
FIGS. 11 and 12 are exemplary diagrams for explaining a user posture recognition solution when a user's position moves, referred to in some embodiments of the present disclosure.
Figure 12:
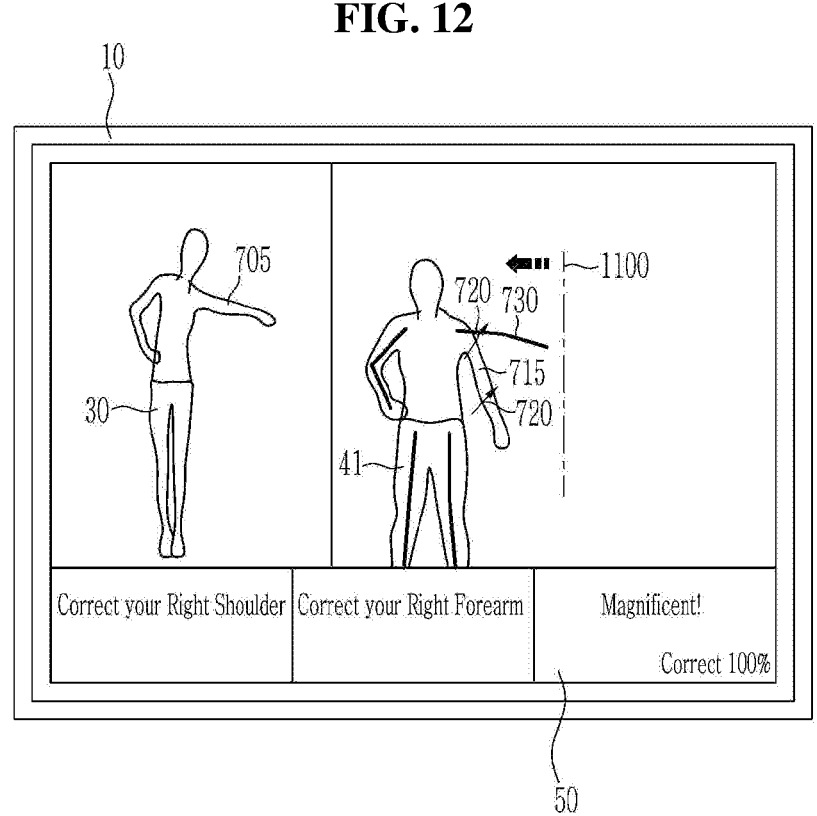

FIGS. 11 and 12 are exemplary diagrams for explaining a user posture recognition solution when a user's position moves, referred to in some embodiments of the present disclosure.

Referring to FIGS. 11 and 12, even if the user moves to the right or left at a central position 1100 of the second region, the apparatus for providing posture guide 100 may identify the tutoring line and the user posture line corresponding to the tutoring line. That is, even if the user walks to the left or right with respect to the central position 1100, the machine learning model of the apparatus for providing posture guide 100 continuously tracks the feature points, and thus, can extract the corresponding feature points and generate the lines.

So far, the method for generating the posture guide information for the user's posture and displaying the information is mainly described. Hereinafter, when the object line shows a repeated error compared to the tutoring target line, an embodiment of a user state determination will be described.

Figure 13:
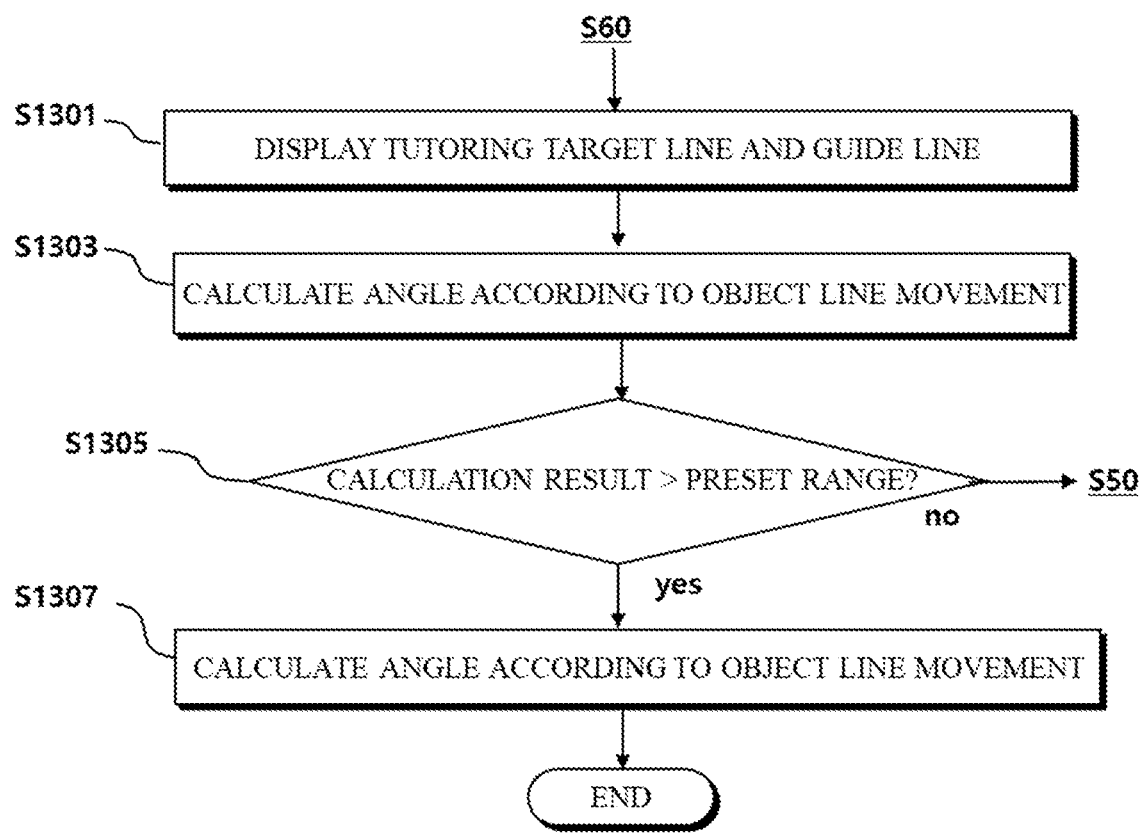
FIG. 13 is a flowchart of a tutoring level adjustment method according to still another embodiment of the present invention.

FIG. 13 is a flowchart of a tutoring level adjustment method according to still another embodiment of the present invention.

If the user's movement does not follow the posture guide information, it may be a deliberate negligence or a problem with a user's physical condition. Hereinafter, it is assumed that a problem occurs in the user's physical condition. The case where a problem occurs in the user's physical condition may be a case where the user cannot abruptly follow the tutoring motion due to an injury or the like of the user or a case where the tutoring motion is difficult for the user or the motion of the rehabilitation exercise is difficult for the user.

Referring to FIG. 13, the apparatus for providing posture guide 100 may display the tutoring target line and the guide line in the second region in step S60 of FIG. 3 (S1301).

Next, the apparatus for providing posture guide 100 may first calculate an angle difference between the object line and the tutoring target line after the movement of the object line occurs (S1303). Here, the first calculation means an angle calculation between the object line corresponding to the posture of the user and the tutoring target line, before adjusting the tutoring level.

The apparatus for providing posture guide 100 may determine whether or not the first calculated angle difference exceeds a preset range (S1305). As a result of the determination, when the first calculated angle difference exceeds the preset range, the apparatus for providing posture guide 100 may adjust the tutoring level (S1307). For example, the apparatus for providing posture guide 100 may generate a first correction tutoring image for the tutoring image. The first correction tutoring image may have a slower speed, fewer times, or a smaller movement angle than the existing tutoring image. That is, the angle of the tutoring target line may be reduced or the length of the guide line may be shortened so that the user can easily follow the tutoring target line. Next, the apparatus for providing posture guide 100 may replace the tutoring image being displayed in the first region with the generated first correction tutoring image and output the generated first correction tutoring image. Accordingly, the motion of the tutor on the tutoring image is changed and output to an image which is easy for the user to follow.

Specifically, in Step S1307, the apparatus for providing posture guide 100 may extract a first correction tutoring line from the first correction tutoring image. Descriptions thereof are the same as those described with reference to FIG. 7, and thus, the descriptions are omitted.

When the angle of the first correction tutoring line is changed by the tutoring motion, the apparatus for providing posture guide 100 may generate a first correction tutoring target line corresponding to the first correction tutoring line having the changed angle and display the first correction tutoring target line in the second region.

Moreover, the apparatus for providing posture guide 100 may second calculate an angle difference between the object line and the first correction tutoring target line after the movement of the object line occurs. In addition, the apparatus for providing posture guide 100 may regenerate posture guide information based on the second calculated angle difference. For example, in the case, after the tutoring level is lowered in Step S1307, the user can easily follow the low tutoring level well. In this case, the apparatus for providing posture guide 100 may second calculate an angle difference between the object line and the first correction tutoring target line, and generate a second correction tutoring image based on the second calculation result. Here, the second correction tutoring image may have a faster speed, more times, or a greater movement angle than the first correction tutoring image. That is, the apparatus for providing posture guide 100 may change the posture guide information for the user posture to increase the tutoring level.

Meanwhile, as a result of the determination in Step S1305, when the first calculated angle difference is within a preset range, the apparatus for providing posture guide 100 may generate the posture guide information, generate the guide line by an angle difference between the tutoring target line and the posture guide information, and display the guide line. In addition, the apparatus for providing posture guide 100 may count the number of times that the first calculated angle difference has a value within a preset range. For example, when the preset range is 10°, in a case where the angle between the object line and the tutoring target line is within 10° and 7 or more times are counted for a total of 10 repetitions, based on this, the apparatus for providing posture guide 100 may determine that the object line and the tutoring target line match to each other.

In the above, for example, the angle difference between the object line and the tutoring target line is described when the first calculated result exceeds the preset range and a problem occurs in the user's physical condition. However, accidental errors, deliberate negligence by the user, or other reasons should be considered. According to still another embodiment of the present invention, the apparatus for providing posture guide 100 may generate the first correction tutoring image. However, the apparatus for providing posture guide 100 may acquire biometric information and check the user's physical condition to improve accuracy of a tutoring level adjustment.

That is, the apparatus for providing posture guide 100 may acquire biometric information of the user from the biometric information recognizer and generate the first correction tutoring image based on the acquired biometric information. For example, the biometric information recognizer may be an EMG measurement device, and may acquire information of the user's physical condition and provide the information to the apparatus for providing posture guide 100.

In addition, the apparatus for providing posture guide 100 may count the number of times the first calculated angle difference has a value within a preset range, and if the counted number of times is less than the preset number, the user's biometric information can be acquired from the biometric information recognizer. The apparatus for providing posture guide 100 may generate the feedback information based on the acquired biometric information.

The methods according to the embodiment of the present invention described above with reference to the accompanying drawings may be performed by execution of a computer program implemented in computer readable code. The computer program may be transmitted to and installed on a second computing device from a first computing device via a network such as the Internet, and thus may be used in the second computing device. The first computing device and the second computing device include a server device, a fixed computing device such as a desktop PC, and a mobile computing device such as a laptop, a smartphone, and a tablet PC.

The embodiments of the present invention are described above with reference to the accompanying drawings. However, a person skilled in the art to which the present invention belongs can understand that the present invention can be embodied in other specific forms without changing a technical spirit or essential features of the present invention. Therefore, it is to be understood that the embodiments described above are exemplary in all respects and not restrictive.

The invention claimed is:

1. A method for providing posture guide performed by an apparatus for providing posture guide by using a machine learning model, the method comprising:
acquiring an image for a user's posture;
displaying a tutoring image in a first region of a display and the acquired image in a second region of the display;
extracting, by using the machine learning model, a feature point from the acquired image;
acquiring user posture information by generating a user posture line corresponding the user's posture based on the extracted feature point;
extracting tutoring lines from the tutoring image;
identifying a posture stop line and motion line out of the tutoring lines;
extracting information of a line corresponding to the posture stop line and object line corresponding to the motion line out of the user posture lines;
extracting dynamic structure information, which is information on lengths, ratios and angles of the posture stop line and the motion line;
generating a tutoring target line based on the extracted dynamic structure information;
generating posture guide information for guiding the user's posture based on the generated tutoring target line;
combining the acquired image and the posture guide information with each other; and
displaying the combination in the second region of the display.

2. The method of claim 1, wherein the generating of the posture guide information for guiding the user's posture comprises,
extracting a tutoring line from the tutoring image,
causing the user posture line to correspond to the tutoring line,
scaling the corresponding user posture line based on the tutoring line, and
generating the posture guide information based on a result of the scaling.

3. The method of claim 1, wherein the combining of the acquired image and the posture guide information with each other and displaying of the combination comprises
displaying the generated tutoring target line in the second region,
generating a guide line for guiding the object line toward the tutoring target line based on an angle difference between the generated tutoring target line and the object line, and
displaying the generated guide line in the second region.

4. The method of claim 3, wherein the displaying of the generated guide line in the second region comprises
changing at least one of a length and a direction in response to a movement of the object line based on the generated tutoring target line and displaying the guide line.

5. The method of claim 3, wherein the displaying of the generated guide line in the second region comprises
determining whether or not the object line and the tutoring target line are matched with each other according to the movement of the object line,
generating feedback information for the user's posture based on a result of the determination, and
displaying the generated feedback information.

6. The method of claim 5, wherein the displaying of the feedback information comprises
changing and displaying a color of the tutoring target line according to the object line and the tutoring target line overlapping each other during a preset time.

7. The method of claim 5, wherein the displaying of the feedback information comprises
calculating first an angle difference between the object line and the tutoring target line after the movement of the object line occurs,
generating a first correction tutoring image for the tutoring image when the first calculated angle difference exceeds a preset range, and
replacing the tutoring image displayed in the first region with the first correction tutoring image and outputting the replaced first correction tutoring image.

8. The method of claim 5, wherein the determining of whether or not the object line and the tutoring target line are matched with each other comprises calculating first an angle difference between the object line and the tutoring target line after the movement of the object line occurs, counting the number of times the first calculated angle difference has a value within a preset range, and determining whether or not the object line and the tutoring target line are matched with each other based on the counted number of times.

9. The method of claim 7, further comprising:

extracting a first correction tutoring line from the first correction tutoring image;

generating, when an angle of the first correction tutoring line is changed by a tutoring motion, a first correction tutoring target line corresponding to a first correction tutoring line having the changed angle;

displaying the generated first correction tutoring target line in the second region;

calculating second an angle difference between the object line and the first correction tutoring target line after the movement of the object line occurs; and regenerating the posture guide information based on the second calculated angle difference.

10. The method of claim 9, wherein the regenerating of the posture guide information includes generating a second correction tutoring image for the tutoring image when the second calculated angle difference is within a preset range.

11. The method of claim 7, wherein the generating of the first correction tutoring image comprises acquiring biological information of the user from a biological information recognizer, and generating the first correction tutoring image based on the acquired biological information.

12. The method of claim 8, wherein the determining of whether or not the object line and the tutoring target line are matched with each other based on the counted number of times comprises acquiring biological information of the user from the biological information recognizer when the counted number of times is less than a preset number of times, and the generating of the feedback information for the user's posture comprises generating the feedback information based on the acquired biological information.

13. A posture guide provision program combined with a computing device and stored in a recording medium, the program executing:

acquiring an image for a user's posture;

displaying a tutoring image in a first region of a display and the acquired image in a second region of the display;

extracting, by using a machine learning model, a feature point from the acquired image;

acquiring user posture information by generating a user posture line corresponding the user's posture based on the extracted feature point;

extracting tutoring lines from the tutoring image;

identifying a posture stop line and motion line out of the tutoring lines;

extracting information of a line corresponding to the posture stop line and object line corresponding to the motion line out of the user posture lines;

extracting dynamic structure information, which is information on lengths, ratios and angles of the posture stop line and the motion line;

generating a tutoring target line based on the extracted dynamic structure information;

generating posture guide information for guiding the user's posture based on the generated tutoring target line;

combining the acquired image and the posture guide information with each other; and displaying the combination in the second region of the display.

14. An apparatus for providing posture guide comprising:

one or more processors;

a camera which acquires an image for a user's posture;

a display which displays a tutoring image in a first region and displays the acquired image in a second region;

a memory which loads a computer program executed by the processor; and a storage which stores the computer program, wherein the computer program comprises an operation of extracting, by using a machine learning model, a feature point from the acquired image, an operation of acquiring the user posture information by generating a user posture line corresponding to the user's posture based on the extracted feature point, an operation of extracting tutoring lines from the tutoring image;

an operation of identifying a posture stop line and motion line out of the tutoring lines;

an operation of extracting information of a line corresponding to the posture stop line and object line corresponding to the motion line out of the user posture lines;

an operation of extracting dynamic structure information, which is information on lengths, ratios and angles of the posture stop line and the motion line;

an operation of generating a tutoring target line based on the extracted dynamic structure information;

an operation of generating posture guide information for guiding the user's posture based on the generated tutoring target line;

an operation of combining the acquired image and the posture guide information with each other; and an operation of displaying the combination in the second region of the display.

* * * * *